United States Patent [19]
Taki et al.

[11] Patent Number: 5,728,582
[45] Date of Patent: Mar. 17, 1998

[54] MONITORING METHOD OF STAIN SOLUTION FOR PARTICLE ANALYSIS AND CALIBRATION METHOD OF PARTICLE ANALYSIS

[75] Inventors: Miki Taki; Yasuaki Kojima, both of Hitachinaka, Japan

[73] Assignee: Hitachi, Ltd., Tokyo, Japan

[21] Appl. No.: 423,213

[22] Filed: Apr. 17, 1995

[30] Foreign Application Priority Data

Apr. 21, 1994 [JP] Japan .................................. 6-082838

[51] Int. Cl.$^6$ ............................................... G01N 31/22
[52] U.S. Cl. ......................................... 436/10; 436/8
[58] Field of Search ................................ 436/10, 8, 16

[56] References Cited

U.S. PATENT DOCUMENTS

| | | |
|---|---|---|
| 3,961,039 | 6/1976 | Sternheimer . |
| 4,331,862 | 5/1982 | Ryan . |
| 4,338,024 | 7/1982 | Bolz et al. . |
| 4,774,189 | 9/1988 | Schwartz ................... 436/10 |
| 4,786,165 | 11/1988 | Yamamoto et al. . |

FOREIGN PATENT DOCUMENTS

| | | |
|---|---|---|
| 305536 | 3/1989 | European Pat. Off. . |
| 314293 | 5/1989 | European Pat. Off. . |
| 5-40118 | 2/1993 | Japan . |
| 6-102152 | 4/1994 | Japan . |
| 2172104 | 9/1986 | United Kingdom . |
| 81/03224 | 11/1981 | WIPO . |

*Primary Examiner*—Lyle A. Alexander
*Attorney, Agent, or Firm*—Fay, Sharpe, Beall, Fagan, Minnich & MCkee

[57] ABSTRACT

Sample fluids including biological particles are mixed with a stain solution, and stained biological particles are fed into a flow through cell. Still frame images of the particles flowing through the flow-through cell are photographed by a television camera, and are processed for particle classification. Prior to such processing of biological particle images, a calibration coefficient is calculated using reference particles. The reference particles may include polystyrene resin which contains functional radicals such as sulfonic radicals, and are stained by mixing the suspended fluid containing these reference particles with the stain solution. The calibration coefficient is calculated according to the information on the stain in the still frame images, and is used to calibrate biological particle data.

14 Claims, 6 Drawing Sheets

MONITORING METHOD OF STAIN SOLUTION FOR PARTICLE ANALYSIS AND CALIBRATION METHOD OF PARTICLE ANALYSIS

BACKGROUND OF THE INVENTION

The present invention relates to a method of monitoring a stain solution in analyzing particles suspended in fluids, as well as a method for calibration. Two methods are known to analyze and classify the particles in biological fluid samples including blood and urine; a method of forming smeared specimens on microscope slide glass, and a method of using a flow cytometer wherein analysis is made by flowing suspended fluid on the flow through cell.

In the method using a flow cytometer, a method has been proposed, wherein fluid samples are fed to the flow through cell to get still frame images of the particles; the method is proposed to solve the problem involved in the difficulty of classifying particles according to morphological features. Examples of such a method include those disclosed in U.S. Pat. No. 4,338,024 and U.S. Pat. No. 4,786,165, according to the U.S. Pat. No. 4,338,024, samples are fed to the flow through cell having the passage of a special configuration, and still frame images are photographed by the television camera, thereby analyzing the particles in the samples according to the images. The U.S. Pat. No. 4,786,165 discloses two optical systems: an optical system to photograph still frame images and an optical system to detect particles passing through inside the flow through cell.

In the flow cytometer or particle analyzer, on the other hand, the standard solution containing the immobilized erythrocyte or latex particles is used to check the repeatability of the number of particles detected in the apparatus, and electric signals are used to calibrate electric drifts and changes in the amount of light of the microscope.

In the analyzer which classifies particles by obtaining still frame images, biological particles in the samples are stained before samples are fed to the flow through cell. The pigment of stain solution, however, is subjected to gradual oxidization and the physical properties undergo changes after opening of the stopper, with its dyeing capacity reduced with the lapse of time. The reduction of dyeing capacity will deteriorate accuracy of particle analysis, resulting in increase in the number of particles which cannot be identified.

SUMMARY OF THE INVENTION

Change in stain concentration is caused not only by deterioration of stain solution with time after opening of the stopper but also by the temperature and humidity environment of the day as well as by storage conditions. However, the operator is incapable of handling such changes When failure has occurred to the stain solution discharge mechanism due to expiration of the service life of the stain solution, failure of the apparatus is detected only during measurement of the patient sample.

An object of the present invention is to provide a calibration method of reducing the impact of the changes in stain solution on the result of measurement for particle analysis.

Another object of the present invention is to provide a monitoring method of allowing the particle staining capacity of the stain solution to be checked.

A further object of the present invention is to provide a method of calibrating the size according to the size of the particles to be analyzed.

A still further object of the present invention is to provide a method of checking if the channel system where sample fluids flow is properly functioning or not.

The method of monitoring the stain solution for particle analysis according to the present invention includes the steps of (1) using stain solution to stain the reference particles which are formed by bonding the functional radical which can bind with the pigment ion to the granular base material comprising the artificial material, (2) forming images of the reference particles by feeding the stained reference particles to the flow through cell, and (3) monitoring the concentration of stain obtained from the images of the reference particles.

The calibration method for particle analysis according to the present invention includes the steps of (1) using stain solution to stain the reference particles which are formed by bonding the functional radical which can bind with the pigment ion to the granular base material comprising the artificial material, (2) forming images of the reference particles by feeding the stained reference particles to the flow through cell, (3) calculating the calibration coefficient based on the information on stain concentration obtained from the images of the reference particles, and (4) calculation of the calibration coefficient to stain the tested particles in sample fluids and to process the images of tested particles.

The functional radical in the reference particles provides the particle base material with an acid or basic property, and allows the pigment ion to bind with the particles in the stain solution. The functional radical is selected from among the sulfonic acid group, carboxyl group, hydroxyl group, chloro group, chloromethyl group, quarternary ammonium base and amino group, while the base material of the reference particles is selected from among a copolymer of polyethylene, styrene and divinyl benzene, a copolymer of styrene and butadiene, polyvinyl toluene and silica gel.

According to the preferred embodiment of the present invention, the stain regulator ion which competes with the pigment ion in the solution to bind with the functional radical is added into suspended fluids containing reference particles. The preferred embodiment of the present invention includes the steps of (1) selecting diameters between 2 to 160 μm for two or more sizes of the reference particles to be suspended in a suspend fluid, and (2) calculating the calibration coefficient based on the size information obtained from the images of said reference particles.

Furthermore, the preferred embodiment of the present invention also includes the steps of (1) feeding a suspended fluid containing the reference particles to the flow through cell at a specified feed volume, and (2) measuring the number of reference particles flowing through the flow through cell at specified time intervals.

DESCRIPTION OF THE PREFERRED EMBODIMENT

Figure 6:
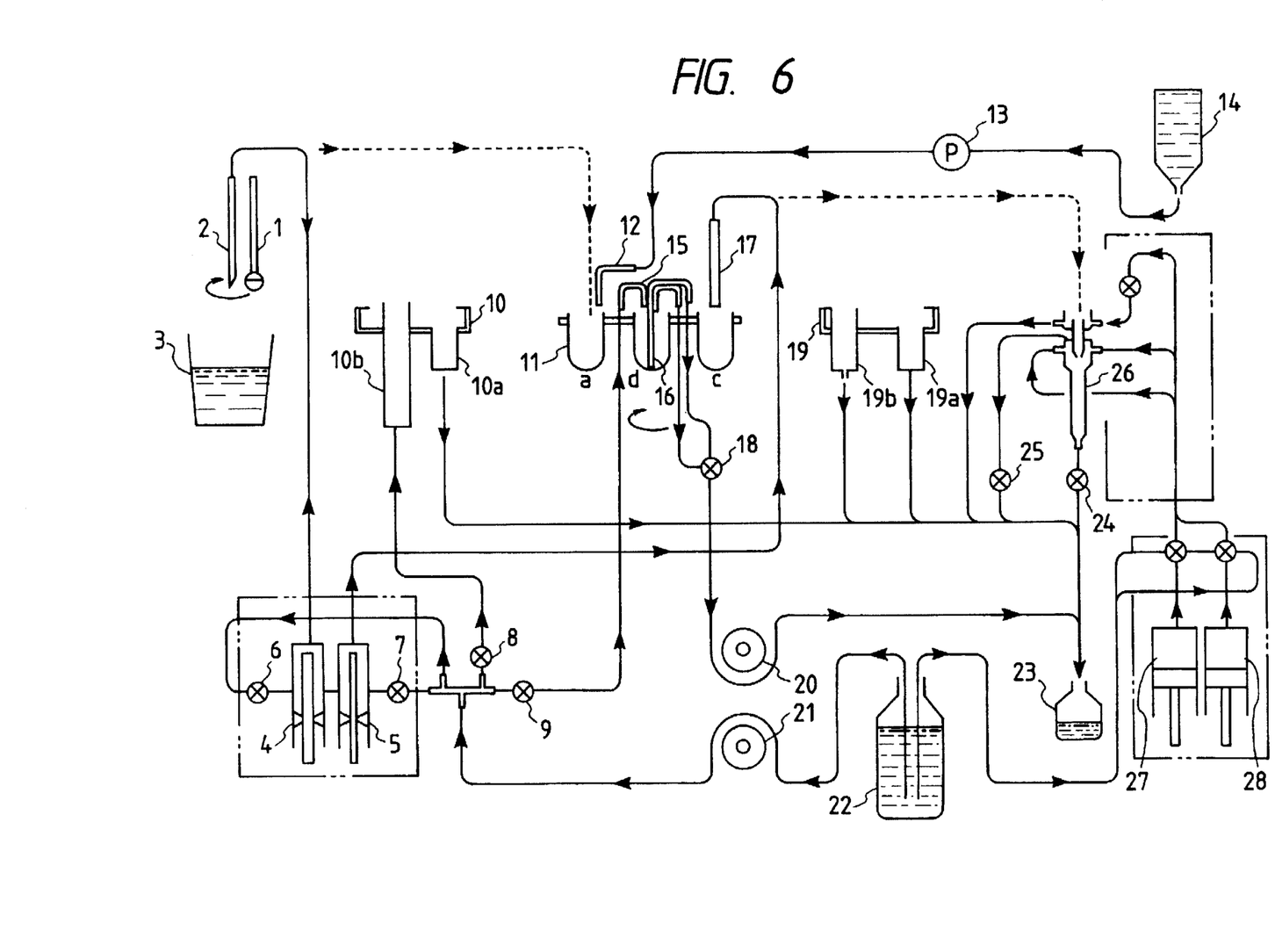
FIG. 6 illustrates the channel of the particle analyzer as one embodiment according to the present invention.

The following describes the channel for analyzing the biological particles in sample fluids with reference to FIG. 6: Firstly, sample containers storing such samples as urine are Set on the Sample table (not illustrated), and the START key on the operation panel 46 (FIG. 7) is pressed. Agitator rod 1 is rotated so that the residue will be uniform, and the sampling pipette nozzle 2 is put into urine sample 3. At the same time, syringe 4 is driven to suck a specified amount. Stain solution 14 is connected to the apparatus, and stain solution pump 13 is driven to discharge a specified amount of urine into the stain bath 11 at position (a) from the stain solution discharge nozzle 12; then the urine sample 3 is discharged into the stain bath 11 through pipette nozzle 2. In this stage the sediment is stained by stain solution 14.

The pipette nozzle 17 for direct sampling is shifted to the stain bath 11 at position (c), and, at the same time, the syringe 5 is driven to suck a specified amount of the stained urine. The nozzle 17 is shifted to the position of the flow cell 26, and is firmly fixed on the flow cell 26, thereby dispensing the sucked stained urine. The sample coming from the nozzle 17 through the flow cell 26 allows a sheath solution, sucked from the sheath liquid tank 22 by driving of the syringes 27 and 28, to flow downward from both sides of the flow cell, and both are discharged into waste tank 23 by opening valves 24 and 25.

After discharging the urine sample, sampling nozzle 2 is shifted to the side (10a) of the nozzle washing bath 10, and discharges into nozzle washing bath 10 the urine sample remaining in nozzle 2, together with the sheath liquid supplied from the tank 22 with the valve 6 opened, by driving of the syringe 4, thereby washing inside the sampling nozzle 2. After that, thereafter shifting the sampling nozzle 2 to the side (10b) of the nozzle washing bath 10, the sheath liquid is supplied from the tank 22 with the valve 8 opened, by the driving of the peristaltic pump 21 to overflow into nozzle washing bath 10 from the bottom side, thereby washing the outside of the sampling nozzle 2.

Similarly, after discharging the stained urine, direct sampling nozzle 17 is shifted to the side (19a) of the nozzle washing bath 19, and discharges into nozzle washing bath 19 the stained urine sample remaining in nozzle 17, together with the sheath liquid supplied from the tank 22 with the valve 7 opened, by the driving of the syringe 5, thereby washing inside the sampling nozzle 17. After that, the nozzle 17 is shifted to the side (19b) of the nozzle washing bath 19, and the sheath liquid supplied from the tank 22 by the driving of the syringe 5 is made to overflow while being discharged into the washing bath 19, thereby washing the outside of the nozzle 17.

The stain bath 11 after sucking the stained urine allows the peristaltic pump 21 to be driven. When the valve 9 is open, sheath liquid coming from the washing nozzle 15 is put into the stain bath 11 at position (d). Then the sheath liquid inside is discharged into the waste tank 23 through the washing nozzle 16 by the driving of the peristaltic pump 20 when the valve 18 is open.

Figure 7:
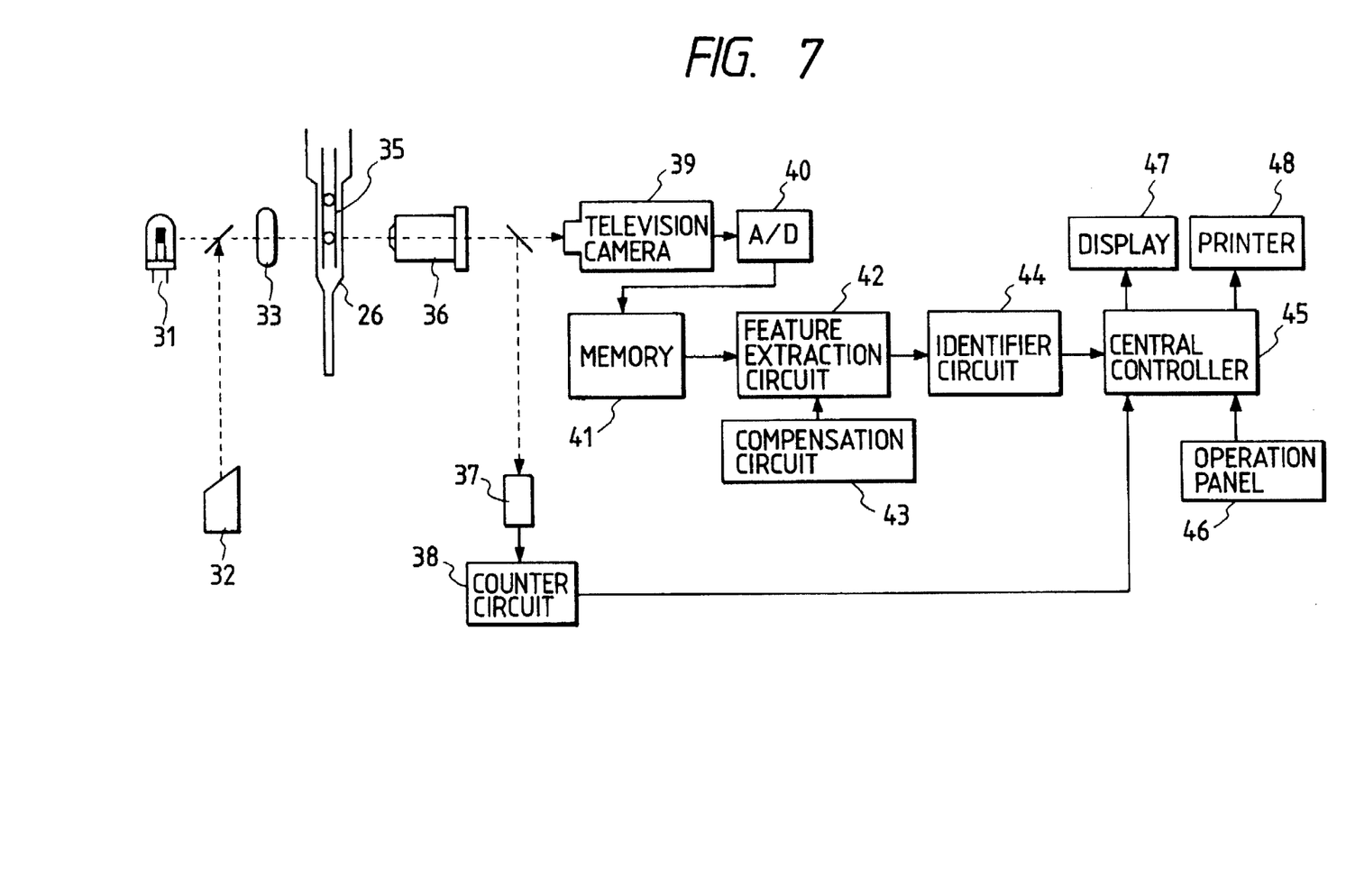
FIG. 7 is a schematic configuration of image processing in the analyzer.

The following describes the particle detecting means, particle photographing means and particle analysis means, with reference to FIG. 7.

The particle photographing means has a microscope function, and causes the flash lamp 31 to emit luminous flux in the form of pulses. The luminous flux propagates along the optic axis of the microscope, and passes through the condenser lens 33 to be concentrated on the sample flowing through the flow cell 26. The pulse of luminous flux irradiated onto the sample flow 35 through flow cell 26 is photographed through object lens 36 of the microscope, and the photographed image is transmit to the television camera 39 which converts the image into an image data signal.

The timing of emitting light from the flash lamp in the particle detecting means is controlled by the detecting signal of the particle detecting means. The semiconductor laser light source 32 is normally lit, and the particle detector 37 observes the particles in the sample passing through the detecting area at all times. When particles have passed by and the particle detecting signal resulting from scattered light has exceeded the specified level, they are judged by the controller 45 as particles to be image processed; then flash lamp 31 lights up and the image is photographed.

The particle detecting means has a particle counter circuit 38 which counts the particles detected within a specified time period, compares it to the preset number and transmits the information to the central controller 45.

The particle analyzing means has (1) an A/D converter 40 which converts into the digital signal the image data transmitted to the television camera 39, (2) an image memory 41 which stores data into the specified address based on the signal coming from the A/D converter 40, (3) a feature extraction circuit 42 which implements graphic processing based on the signal coming from the image memory, (4) a compensatory circuit 43 for image data, (5) an identifier circuit 44 for classification, and (6) a central controller 45 which provides (a) storage of photographing conditions for television camera 39, conditions for feeding the sample fluid of the flow cell 26, and processing results from the identifier circuit, (b) a display on the display unit (liquid crystal display) 47, and (c) an output to the printer 48. Furthermore, operation panel 46 is provided to input commands for analysis parameter setup, data correction and mechanism system maintenance. The analyzer of FIG. 7 uses the information on form and stain concentration as identifier parameters for particle analysis.

Material for the artificial particles includes a copolymer of polystyrene, styrene and divinylbenzene, polyvinyl toluene, silica gel, and a copolymer of styrene and butadiene. These particle products having a diameter of 3 to 300 μm are extensively available on the market, particles are used an two or more forms: spherical, elliptical, and rod. The particle surfaces are provided with concavities and convexities to ensure efficient binding with functional radicals. This is well known as filler for liquid chromatography. Latex or similar particles having no concavities and convexities on the surface are disadvantageous in that only a limited number of functional radicals can bind on the surface, stain concentration is low, and staining takes a long time.

Types of functional radicals used include the sulfonic acid group ($-SO_3H$), hydroxyl group ($-OH$), chloro group ($-Cl$), quarternary ammonium base ($-C_2Ne(CH_3)_3Cl$), carboxyl group (—COOH), amino group (—NH$_2$), and chloromethyl group (—C$_2$Cl).

When analyzing biological components, mainly sediments in urine, main sediments include bacteria (2 μm), red blood cells (6 to 20 μm), white blood cells (6 to 20 μm), epthelial cells (20 to 100 μm), and casts (100 to 169 μm or longer), each differing in size. Sediments comprising such different types and sizes coexist in one specimen of urine. Accordingly, the particle image analyzer uses two types of magnifications for photographing; therefore, it is preferred to correct identifier parameters in two phases.

For stain solution for urine sediment, the Sternheimer-Marbin method (hereinafter referred to as the "SM method") and the Sternheimer method (hereinafter referred to as the "S method") are extensively used. Acid pigment safranine —O(C$_2$OH$_{19}$ClN$_4$) and basic pigment crystal violet (C$_{25}$H$_{30}$ClN$_3$) are mixed in the SM method, while acid pigment pyronin B (C$_{42}$H$_{52}$C$_{18}$Fe$_2$N$_4$O$_2$) and basic pigment Alcian Blue (C$_{32}$H$_{16}$N$_6$Cu) are mixed in the S method. Thus, the solution prepared in this manner has two types of peak wavelengths provided by acid and basic pigments (red for acid pigment and blue for basic pigment), allowing color identification according to components. The basic pigments further include Evans blue (C$_{34}$H$_{24}$N$_6$Na$_4$O$_{14}$S$_4$), trypan blue (C$_{34}$H$_{24}$N$_6$Na$_4$O$_{14}$S$_4$) and methylene blue (C$_{16}$H$_{18}$ClN$_3$S.3H$_2$O), and the acid pigments further include erythrocin B (C$_{20}$H$_6$I$_4$Na$_2$O$_5$). These pigments resolve in water, and satin the sediment when mixed with biological components of urine.

The following describes the preparation of an artificial particle-suspended solution used for particle analysis calibration: Artificial particles are composed of a sulfonic acid group (—SO$_3$H) bound to the particles of a copolymer of styrene and divinylbenzene (having an average particle diameter of 8 μm), and are strongly acid, having a wet specific gravity (g/milliliter) of 1.312 and an exchange capacity (meq/millimeter) of 2.0 or more. Particles of another type are also made of a copolymer of styrene and divinylbenzene, but have an average particle diameter of 40 μm; they are bonded with quarternary ammonium base. These reference particles are strongly acid, having a wet specific gravity (g/milliliter) of 1.312 and an exchange capacity (meq/millimeter) of 2.0 or more.

To prevent these particles from aggregating, 0.1 percent of triton X-100 (polyoxyethylene (10) octylphenylether) is added to them, and particles are suspended so that they wall have a concentration of 250 particles per microliter. This concentration value is gained by preparation on a particle counter. These two types of particle-suspend solution are mixed in equal volumes.

Stain solution is prepared by mixing 2 percent of erythrocin B aqueous solution (WM 880; 0.2×102 mol/liter) and 1 percent of methylene blue aqueous solution (WM 373.5; 2.6×102 mol/liter) at the ratio of 2 to 1, and by filling sediments thereafter. Methylene blue pigment ion binds with acid particles (8 μm) and stains particles in blue, while erythrocin B binds with basic particles (25 μm) to stain them in red. These two types of particles are suspended in the same fluid.

Use of ion exchange filler (available on the market) particles as material may be economical, but tends to be stained in red earlier than the biological components of the urine since the particle surfaces are bound with many functional radicals. Accordingly, the stain regulator ion which can bind with the functional radical one artificial particles is made to be contained in the suspended fluid in advance. This stain regulator ion competes with the pigment ion of the stain solution to bind with the functional radical of the particles, thereby providing a stain concentration close to that of the biological compound, and prolonging the staining time.

Figure 1:
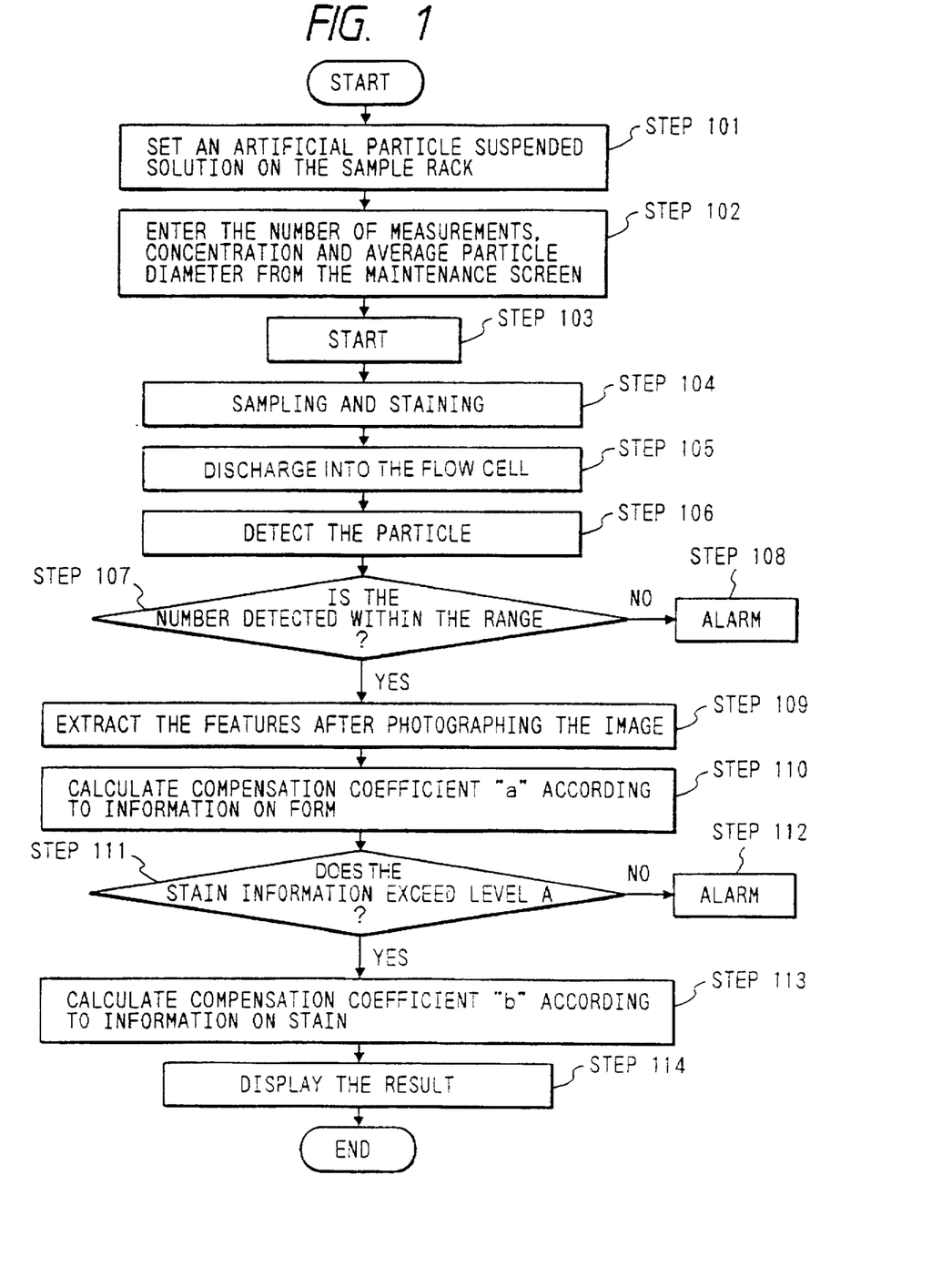
FIG. 1 is a flow chart representing the calibration method of the particle analyzer as an embodiment according to the present invention.

With reference to FIG. 1, the following describes the calibration procedures using the suspension of reference particles.

The reference particle-suspended solution is set on the sample rack (not illustrated), and the number of measurements, particle concentration (per microliter) and average particle diameter (μm) are entered in the computer while observing the maintenance screen; then the START key on the operation panel is pressed. The reference particle-suspended solution is sufficiently mixed by the agitator rod 1, and a specified amount of it is sucked by the sampling nozzle 2 (steps 101 to 103). Then it is discharged into the stain bath 11 containing the stain solution, and staining of reference particles is started. After the lapse of a specified time, direct sampling nozzle 17 sucks the sample containing the stained particles to discharge it into the flow cell 26 (steps 104 and 105).

Then the number of detected particles passing through the particle detection area is measured at preset time intervals. When the measured number has exceeded the preset range, an alarm will be issued, and the alarm contents are indicated on the display unit 47, thereby notifying the operator. Details of checking the channel stability are described later (steps 106 to 108).

When detected particles have reached the photographing area in the channel, the still frame image is photographed, thereby extracting the features of the form information. Since the artificial particles are different in size, 50 to 100 still frame images are photographed and the average of the particle diameters is obtained (in step 109). This average value becomes the average diameter to be entered on the maintenance screen. Compensation coefficient "a" is calculated by comparison with the size of the screen preset in the apparatus (step 110).

Artificial particles can be prepared in spherical, elliptical, rod and indeterminate forms. In this case, information on forms such as particle diameter, shorter and longer diameters, circumferential length and area provide important factors. Details of the form information will be discussed later.

Next, features of information on the stain concentration of still frame images are extracted. Since there are variations in particle stain concentrations similar to the case of forms, still frame images of 50 to 100 particles are photographed to take the average stain concentration. When the average stain concentration is below the low level of the set values in the apparatus (hereinafter referred to as "level A"), the service life of the stain solution is already expired or the stain discharge mechanism is faulty in many cases. In these cases, stain concentration is extremely low, resulting in poorer analysis accuracy despite compensation efforts. In these cases, an alarm is issued to prompt the user to check the quality of the stain solution and discharge mechanism and to protect the equipment by preventing the routine inspection from being started (step 111 to 112).

When the average stain concentration is above the level A, it is compared with the standard stain concentration of the reference particles preset in the equipment, thereby calculating the compensation coefficient b for stain concentration (step 113). Compensation for stain concentration will be discussed later.

Lastly, the following results are displayed on the maintenance screen; average concentration for the number detected (microliter), range, CV (%), average stain concentration, and difference from standard stain concentration. Contents are displayed when the alarm has occurred (step 114). The steps described hereinbefore are of the calibration method in which the reference particles are used.

These compensation coefficients are stored in the memory, and the most updated compensation coefficient is adopted. Unless otherwise specified, Calibration of the equipment is preferred to be completed when consideration is given to optical and electrical variations and variations of stain concentration, but may be done during routine tests.

Figure 2:
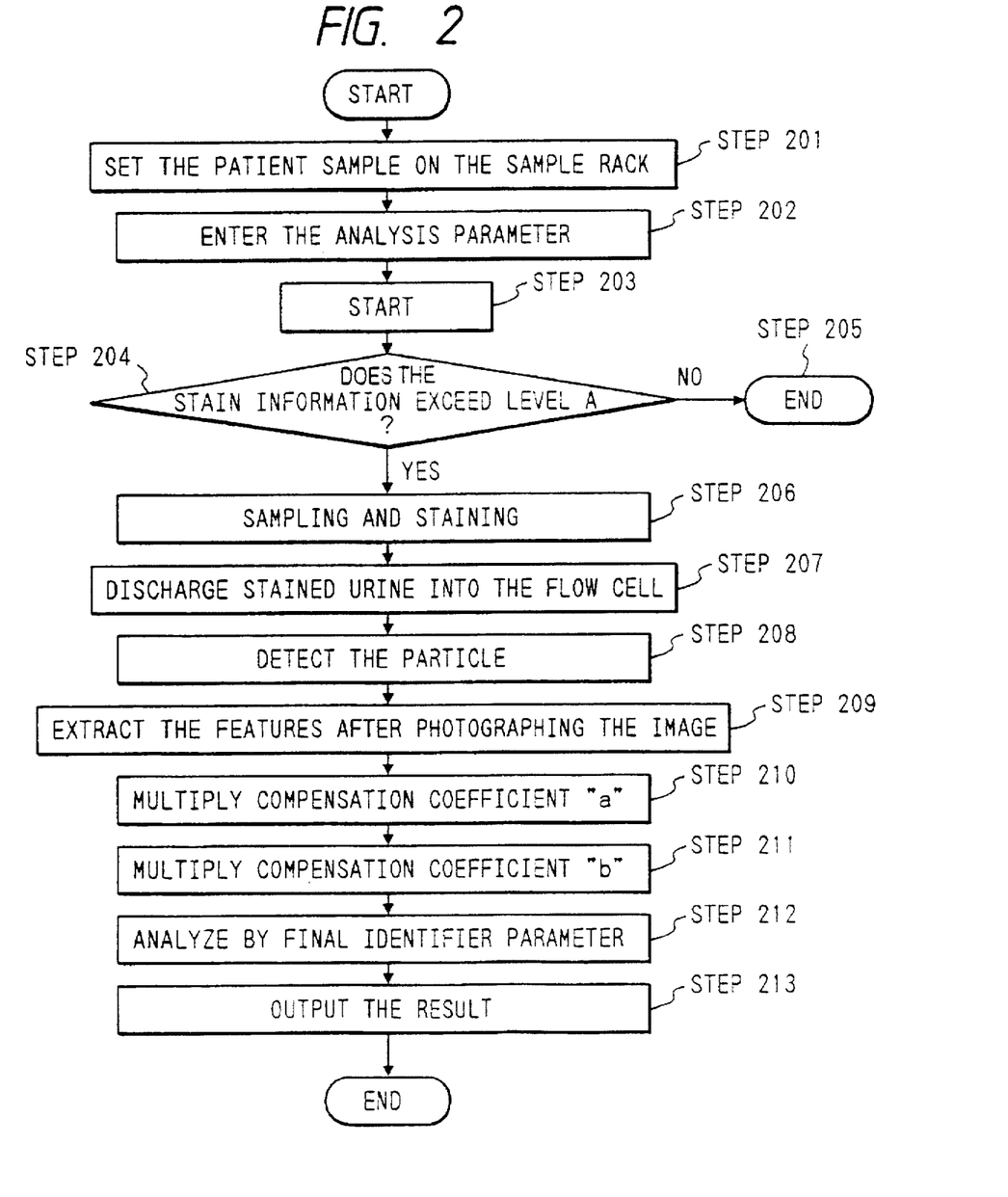
FIG. 2 is a flow chart for executing routine tests of sample fluids.

The following describes the routine test procedure according to the flow chart given in FIG. 2.

The urine sample of the patient is set on the sample rack (not illustrated), and such parameters as classification items required for analysis, specimen number and display unit are entered in the computer; then the START key on the operation panel is pressed (steps 201 to 203). The system checks if the newest calibration result of the average stain concentration at this time exceeds level A or not. If the result is lower than level A, sampling is stopped (steps 204 and 205); whereas routine inspection is started if it is above level A.

The urine sample of the patient is stirred by an agitator rod so that the sediment and urine will be mixed uniform. A specified amount of the sample (800 to 1000 microliters) is sucked through sampling nozzle 2, and is discharged into the stain bath 11 where stain solution (100 to 120 microliters) has been discharged; then staining is initiated. After the lapse of a specified time, stained urine is dispensed into the flow cell 26 through the nozzle 17 (steps 206 and 207).

If the detection signal of the particle having passed through the particle detecting area in the channel is over a specified level, that particle is identified as sediment component. When it has passed through the image pickup area in the channel, the flash lamp lights up and the still frame image is photographed, and information on form and stain concentration is extracted as features from that still frame image (steps 208 and 209). The parameter to identify the size of the tested particle of the urine sample (particle diameter) is multiplied by compensation coefficient "a", and the parameter to identify stain concentration multiplied by compensation coefficient "b", thereby getting the final identifier parameter (steps 210 and 211). This final parameter is used to analyze each sediment component, to memorize the type and amount of the sediment component in the patient urine sample, to display it on the display unit 47 and to print it out by printer 48 (steps 212 and 213).

To check the channel stability, particle detection is conducted using the artificial particle-suspended solution as a sample. As the conditions in this case, the sample flow rate is 0.25 microliter per sec. and the sample particle concentration is 500 particles per microliter. The artificial particle-suspended solution is used because, although there are two types of particle diameters, when particles are detected, they are counted as one type of particle. If the channel system is stable, the concentration is estimated at about 125 particles per sec. ±13 particles (fluctuation: ±10%). However, 125 particles per sec. (fluctuation: ±20%) is selected as the set range, with consideration given to the particle concentration in the sample and variations of sheath flow.

Figure 3:
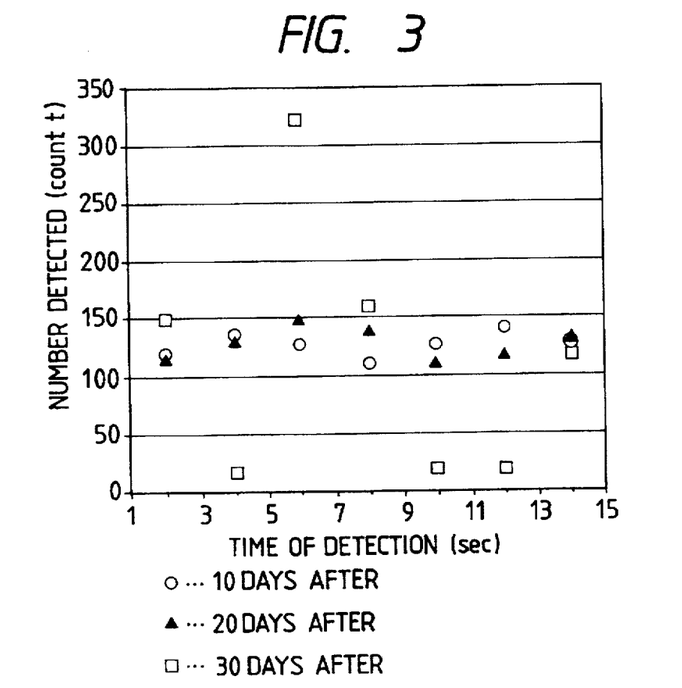
FIG. 3 is a graph showing the result of measuring the channel system stability.

FIG. 3 illustrates the actual data. Contamination of the flow cell is considered to be one of the reasons why the sample flow as unstable. So FIG. 3 shows the data taken for 30 days by suspending washing of the channel by detergent. The white circle shows the case where the artificial particle-suspended solution is fed for particle detection 10 days after, the black triangle shows the case where it is fed 20 days after, and the square shows the case where it is fed 30 days after; then the number of the particles detected is added up in increments of 2 seconds in each case. The cases of 10 days after and 20 days after are within the set range, and the channel is also stable. However, the case of 30 days after far exceeds the set range, the number detected being close to 0 (zero) at times or over 300; thus, the case is unstable with big fluctuations. This is an example where the channel is unstable due to a contaminated flow cell.

The criteria for channel system stability check have been set as follows: The number of particles detected is added up at intervals of 1 to 2 sec. of particle detection. Every fluctuation is the average number ±20% or less. The case where the number checked is below one third of the average number is measured one or more times, and the case where the number checked is over three times the be average number is also measured one or more times. An alarm is given according to judgment to prompt the user to check the channel system (flow cell and direct sampling); this makes it possible to check whether the channel before routine inspection is appropriate or not, and whether cleaning of the channel is required or not.

Figure 4A:
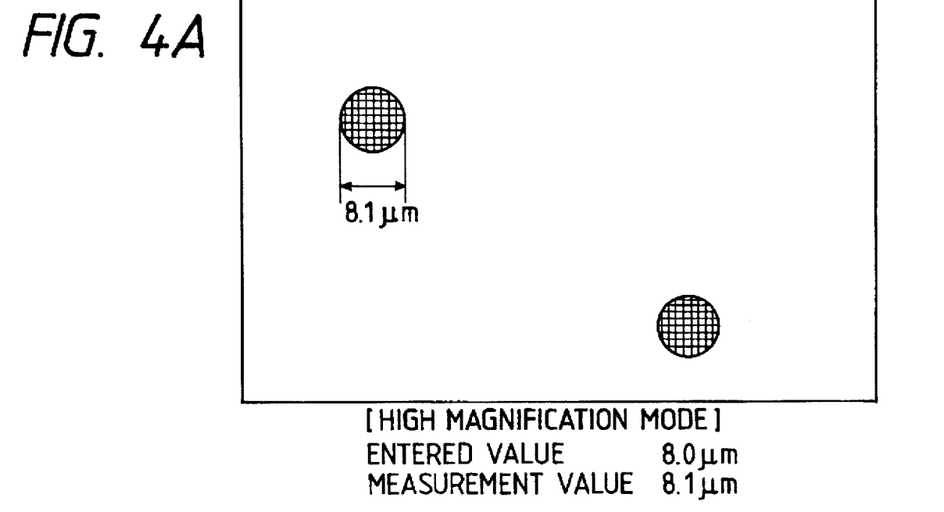
FIGS. 4A and 4B are schematic representations of the still frame images of reference particles.
Figure 4B:
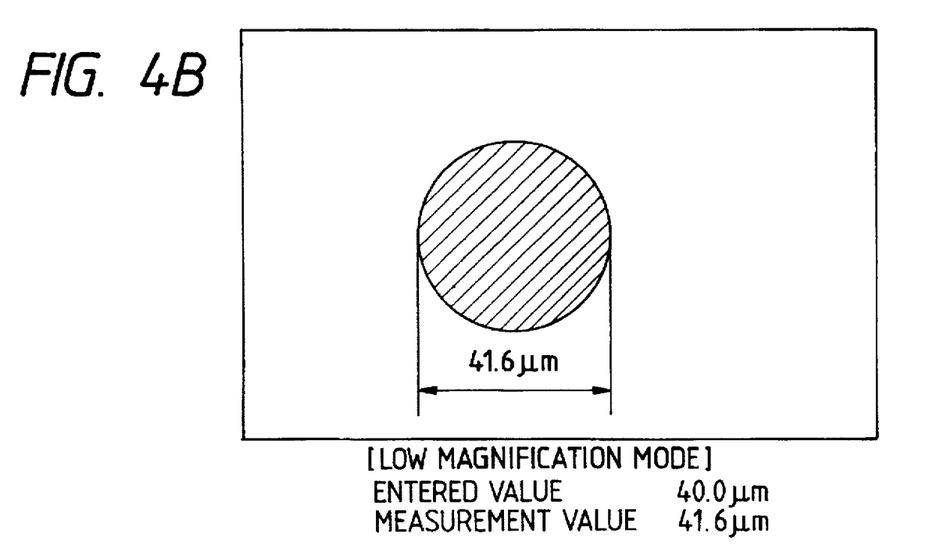

FIGS. 4A and 4B are schematic diagrams showing still frame images photographed by using a reference-suspended solution. To extract form information features, the diameters of 50 to 100 particles for each type of particle having different sizes are measured from still frame images according to the size of the image set theoretically in the equipment, thereby obtaining the average value (8.1 μm). This average value is compared with the average particle size (8.0 μm) input on the maintenance screen, thereby calculating the compensation coefficient which is used to multiply the value representing the urine sample of the patient. In this case, compensation coefficient "a" in FIG. 4A is 8.0/8.1=0.988, while compensation coefficient "a" in FIG. 4B is 40.0/41.6=0.962.

As discussed above, the sediment components in the urine sample differ greatly, magnifications must be changed when photographing particles having a diameter of 30 μm or less, and those having a greater diameter. Particles having other diameters in the artificial particle suspended solution are photographed in lower magnification mode. Compensation coefficient is calculated as in the case of a higher magnification mode. Thus, more accurate information on form is ensured by using different compensation coefficients according to larger particles and smaller particles.

Biological particles are not only spherical; they have a great variety of forms. When reference particles are considered to have elliptical or rod indeterminate forms, such parameters as shorter diameter, longer diameter, circumferential length and area (not particle diameter) are extracted as features, and they are compensated, thereby ensuring more accurate analysis.

Figure 5:
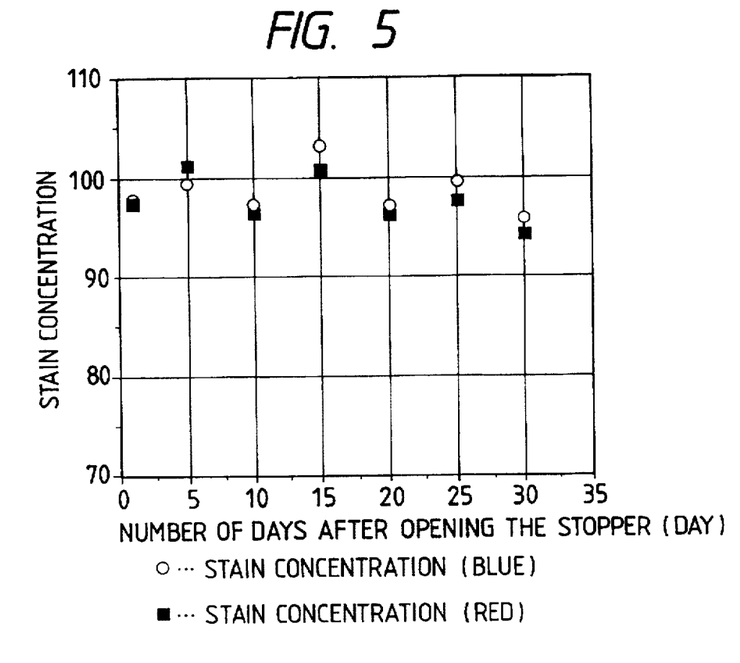
FIG. 5 is a graph illustrating changes in stain concentration after opening of the stain solution stopper.

Lastly, the following describes the compensation for stain concentration: FIG. 5 shows the result of measuring the fluctuation of stain concentration after opening the stopper, using the reference particle-suspended to stain solution. The 8 μm particles are stained in blue, while 40 μm particles are stained in reddish purple. The average concentration of 50 to 100 particles per picture element is obtained for each of them. The stain concentration preset in the equipment is assumed as 100, and measurement has been made 5, 10, 15, 20, 25 and 30 days after opening of the stain solution container stopper. Depending on the components of biological particles, they are stained in red by acid pigment, or in blue by basic pigment. As an identification parameter for analysis, the color balance becomes a major factor for analysis.

The stain capacity of the stain solution greatly varies according to the storage conditions, degeneration after opening the stopper, and the temperature and humidity of the environment. Furthermore, the stain capacity reduction rate depends on the type of pigment. Temperature also has a serious impact; an increase of 10° C. or more is said to increase stain concentration twice. Pigment product lots also have and cause subtle changes.

As given in FIG. 5, the stain concentration undergoes gradual changes after opening of the stain liquid container stopper. Stain concentration also depends on the time of the day. The standard concentration preset in the equipment is set at 100%, and compensation coefficient "b" is calculated for each of the blue and red so that the actual concentration value will be 100. For example, blue stain concentration is 96.4% and compensation coefficient "b" is 100/98=1.04 on the 10th day. The blue stain concentration of the biological component to be analyzed thereafter is multiplied by 1.04 to get the final identification parameter.

When the stain concentration is below 70% of the standard concentration, analysis accuracy will not be improved even by multiplying the compensation coefficient. This is often caused by reduction of discharge amount due to failure of the stain solution discharge mechanism or expiration of the service life of the stain solution. Accordingly, when there is an extreme reduction in concentration, an alarm will be given to prompt the user to check the conditions. This is more effective than compensation.

As discussed above, the use of artificial particles permits selection of rod, elliptical or indeterminate form as well as spherical form in conformity to the target component, and allows two or more types of size from 2 to 160 μm to be prepared. Further, artificial particles present no danger of infection, ensuring less deterioration and easier storage.

Furthermore, staining of reference particles with functional radicals bound on the surface by the stain solution allows information to be supplied on the quality of the stain solution and temperature environment at the time of use. Moreover, since uniform staining is ensured reflecting the staining time and staining capacity, the stain concentration of still optical images and the standard stain concentration are compared to calculate compensation coefficients and to compensate for identifier parameters of stain concentrations in biological particle samples to be analyzed thereafter, thereby ensuring analysis at a specified stain concentration at all times.

The reference particle in the suspended solution can be stained in two or more colors by the combination between the bound functional radical and pigment ion, and two or more colors can be compensated in one type of liquid; particle analysis uses two or more parameters. Therefore, analysis accuracy is improved.

What is claimed is:

1. A method of calibration for particle analysis, comprising the steps of:
   (1) staining reference particles constituted by particle base material bound with functional radicals, the reference particles being contained in a suspension, by binding pigment ions of a stain solution with the functional radicals of the reference particles;
   (2) feeding the reference particles stained in step (1) into a flow through cell;
   (3) forming images of the reference particles in the flow through cell;
   (4) obtaining stain densities from the images formed in step (3);
   (5) calculating an average of stain densities of the images formed in step (3);
   (6) comparing the average calculated in step (5) with a preset level indicating quality of the stain solution;
   (7) generating a stain solution effectiveness signal prompting a user to check the stain solution, when the result of step (6) meets a preset condition; and
   (8) calculating a first calibration coefficient based on the comparison made in step (6).

2. A method according to claim 1, wherein said base material is selected from the group consisting of a copolymer of polystyrene, styrene and divinylbenzene; a copolymer of styrene and butadiene; polyvinyl toluene; and silica gel.

3. A method according to claim 1, wherein the reference particles of the suspension contain first reference particles having a functional radical which causes the first reference particles to be acidic, and second reference particles having a functional radical which causes the second reference particles to be basic.

4. A method according to claim 1, wherein said suspension further contains stain regulator ions which compete with the pigment ions of the stain solution to bind with sad function radicals.

5. A method according to claim 1, further comprising the steps of:
   feeding the suspension containing said reference particles to the flow through cell at a specified flow rate, and
   measuring, more than two times, the number of reference particles flowing through the flow-through cell at specified time intervals.

6. A method according to claim 1, wherein said functional radicals change the pH of the particle base material to a predetermined acid or basic range.

7. A method according to claim 6, wherein said functional radicals are selected from the group consisting of the sulfonic acid group, carboxyl group, hydroxyl group, chloro group, chloromethyl group and quarternary ammonium base.

8. A method according to claim 1, wherein the suspension contains two or more types of reference particles having different respective sizes.

9. A method according to claim 8, wherein two or more of said sizes of said reference particle are diameters selected from the range of 2 to 160 μm.

10. A method according to claim 8, further comprising the step of calculating a second calibration coefficient based on the information of the reference particle sizes, which sizes are obtained from the reference particle images formed in step (3).

11. A method of calibration for particle analysis, comprising the steps of:
   (1) supplying to a stain vessel a reference fluid in which reference particles are suspended, the reference particles being each composed of an artificial particle bound with a functional radical for attracting dyeing ions which are contained in a stain solution for staining test particles in a sample fluid;
   (2) adding a stain solution to the stain vessel, the stain solution containing dyeing ions attracted to the functional radicals to stain the reference particles;

(3) creating still pictures of the stained reference particles with an electronic camera while the stained reference particles flow through a flow through cell;

(4) calculating an average of stain densities of the still pictures created in step (3);

(5) comparing the average calculated in step (4) with a preset level indicating quality of the stain solution; and (6) generating a stain solution effectiveness signal promoting a user to check the stain solution, when the result of step (5) meets a preset condition.

12. The method according to claim 11, further comprising the following steps:

measuring the number of the stained reference particles flowing through the flow through cell; and generating a visual flow stability alarm when the measured number of the stained reference particles is out of a predetermined allowable range.

13. The method according to claim 11, wherein the reference particles are made of an ion exchange resin, and the reference fluid contains ions which compete with the dyeing ions in the stain solution for binding with the functional radicals of the reference particles, such that undue stain is moderated.

14. A method for identifying components of sample, comprising the following steps:

(1) supplying to a stain vessel a reference fluid in which reference particles are suspended, the reference particles being each composed of an artificial particle bound with a functional radical for attracting dyeing ions which are contained in a stain solution for staining test particles in a sample fluid;

(2) adding a stain solution to the stain vessel, the stain solution containing dyeing ions attracted to the functional radicals to stain the reference particles;

(3) creating still pictures of the stained reference particles with an electronic camera while the stained reference particles flow through a flow through cell;

(4) calculating an average of stain densities of the still pictures created in step (3);

(5) comparing the average calculated in step (4) with a preset level indicating quality of the stain solution;

(6) generating a stain solution effectiveness signal prompting a user to check the stain solution, when the result of step (5) meets a preset condition;

(7) calculating a stain calibration coefficient based on the difference between the average calculated in step (4) and a predetermined standard value; and (8) applying an identification parameter modified by using the stain calibration coefficient calculated in step (7) to identify the stained test particles in the sample fluid.

* * * * *